US007696890B2

(12) United States Patent
Bandholz et al.

(10) Patent No.: US 7,696,890 B2
(45) Date of Patent: Apr. 13, 2010

(54) CAPACITIVE DETECTION OF DUST ACCUMULATION USING MICROCONTROLLER COMPONENT LEADS

(75) Inventors: Justin Potok Bandholz, Cary, NC (US); Zachary Benson Durham, Asheboro, NC (US); Clifton Ehrich Kerr, Durham, NC (US); Joseph Eric Maxwell, Cary, NC (US); Kevin Michael Reinberg, Durham, NC (US); Kevin S. Vernon, Durham, NC (US); Philip Louis Weinstein, Apex, NC (US); Christopher Collier West, Raleigh, NC (US)

(73) Assignee: International Business Machines Corporation, Armonk, NY (US)

( * ) Notice: Subject to any disclaimer, the term of this patent is extended or adjusted under 35 U.S.C. 154(b) by 414 days.

(21) Appl. No.: 11/837,982

(22) Filed: Aug. 13, 2007

(65) Prior Publication Data

US 2009/0045967 A1   Feb. 19, 2009

(51) Int. Cl.
*G08B 21/00* (2006.01)
*G01R 27/26* (2006.01)

(52) U.S. Cl. .................. 340/627; 340/617; 340/620; 624/686

(58) Field of Classification Search .............. 340/617, 340/620, 627–628, 612, 616, 606–610; 324/519, 324/548, 663, 672–673, 686–690
See application file for complete search history.

(56) References Cited

U.S. PATENT DOCUMENTS

| 4,183,029 A | 1/1980 | Isayama et al. |
| 4,400,971 A | 8/1983 | Tassicker |
| 5,247,827 A | 9/1993 | Shah |
| 5,457,396 A | 10/1995 | Mori et al. |
| 7,129,847 B2 * | 10/2006 | Right et al. .................. 340/628 |
| 7,262,704 B2 * | 8/2007 | Shetty et al. ................. 340/627 |
| 2001/0048312 A1 | 12/2001 | Nakamura |
| 2007/0044579 A1 | 3/2007 | Yamaguchi et al. |

FOREIGN PATENT DOCUMENTS

JP   61-186846   8/1986

* cited by examiner

*Primary Examiner*—Benjamin C Lee
*Assistant Examiner*—Michael Shannon
(74) *Attorney, Agent, or Firm*—Cynthia G. Seal; Jeffrey L. Streets

(57) ABSTRACT

A system and method are used for electronically detecting the accumulation of dust within a computer system using a capacitive dust sensor. The dust detection system may be implemented on a smaller computer, such as an individual PC, or in a more expansive system, such as a rack-based server system ("rack system") having multiple servers and other hardware devices. In one embodiment, each server in a rack system includes a capacitive sensor responsive to the accumulation of dust. The capacitive sensor may include one or more capacitive plates integral with a heatsink. As dust collects on the capacitive plates, the capacitance increases. When a capacitance setpoint is reached, indicating the dust has reached a critical level, an alert is generated. The alerts may be received by a management console for the attention of a system administrator. Each alert may contain the identity of the server generating the alert, so that the system administrator knows which server(s) are to be removed for cleaning.

14 Claims, 5 Drawing Sheets

CAPACITIVE DETECTION OF DUST ACCUMULATION USING MICROCONTROLLER COMPONENT LEADS

BACKGROUND OF THE INVENTION

1. Field of the Invention

The present invention relates to the detection and removal of dust in electronic systems.

2. Description of the Related Art

Airflow is commonly used to remove heat generated by components within a computer. For example, an individual PC typically includes one or more on-board cooling fans enclosed within the housing to cool the processors, power supply, memory, and other internal components. In more expansive computer systems, such as rack-based blade computer systems having multiple servers, one or more blower modules are supported on a multi-server chassis to generate airflow through the servers and other components. Despite efforts to keep a computer center clean and filter dust out of the air, the airflow used to cool a computer carries some amount of dust, which accumulates over time on internal components of the computer. The electrostatic charge generated by some components can even attract dust to those components, thereby increasing the amount and rate of dust deposited.

Unfortunately, the accumulation of dust in a computer system can cause problems. Excessive dust build-up can reduce system performance, increase the rate at which components fail, and reduce overall system reliability. Dust can also interfere with operation of moving parts, such as fan blades and mechanical connectors, and reduce the reliability of electrical components, such as by collecting between electrical contacts in electrical connectors. Dust can even give off an unpleasant odor when heated through contact with hot components.

The amount of dust that accumulates in a hardware device is typically not apparent without removing it and opening it up. Manually inspecting hardware for dust is inefficient, usually necessitating the removal of the hardware from the chassis. In many cases, the system must be off line for a person to physically disassemble and clean out the system. An improved dust detection system and method are therefore needed. Improvements in the speed and ease of detecting dust accumulation would be especially desirable in larger computer systems such as rack systems having numerous servers and other hardware components. It would be particularly desirable to have a system and method that would automatically detect the accumulation of dust.

SUMMARY OF THE INVENTION

The present invention provides systems and methods for detecting dust within an electronic system, such as within a computer system.

One embodiment provides a dust detection system for detecting the accumulation of dust in an air-cooled hardware device. A device housing includes an air inlet and an air outlet. An airflow source is configured for generating airflow through the device housing from the air inlet to the air outlet. A microcontroller disposed in the device housing includes a plurality of input leads and a built-in capacitance sensor configured for generating a signal in relation to the capacitance between at least two of the input leads. The capacitance sensor is sensitive to accumulation of dust between the at least two input leads.

Another embodiment provides a method of detecting dust within a hardware device. Airflow is generated through a housing of the hardware device. The capacitance between at least two input leads of a microcontroller disposed within the hardware device is sensed. A change in capacitance is detected between the at least two input leads consistent with the deposition of dust between the leads. A signal is generated responsive to the change in capacitance.

Other embodiments, aspects, and advantages of the invention will be apparent from the following description and the appended claims.

DETAILED DESCRIPTION OF PREFERRED EMBODIMENTS

The present invention provides a system and method for electronically detecting the presence of dust within a computer system using a microcontroller ("chip") having built-in capacitive sensing technology. One of the chips customarily included with a computer system, such as the CPU, Ethernet Controller, Memory Controller, IO Controller, or Video Controller, may be modified or re-designed to include a capacitive-sensing subsystem. Alternatively, a separate chip having built-in capacitive sensing technology could be added to an existing system configuration. The dust detection system may be implemented in a stand-alone computer, such as an individual PC, or in a more expansive system, such as a rack-based blade server system ("rack system") having multiple blade servers and other hardware devices. The chip is configured to detect a change in capacitance consistent with the accumulation of dust. When the capacitance reaches a setpoint, the chip generates an alert. This provides automatic detection of dust within a computer system so that hardware need not be manually inspected for dust. This saves time and money, and wear and tear on components such as device connectors.

In one embodiment, each server in a rack system may receive one of the chips having a capacitive sensing subsystem. Each chip is placed on a motherboard of the respective server, in the path of the airflow through the server. Firmware is provided to enable the detection of capacitance changes caused by dust accumulation. Each chip monitors the capacitance between two adjacent input leads (which may be pins or terminals) on the chip, and is sensitive to changes in capacitance as dust accumulates between the adjacent input leads. The leads are spaced within about 1 mm of each other, and the chip is oriented with the two adjacent leads upstream of the body of the chip. In response to reaching or exceeding a capacitance setpoint, the chip generates an alert, such as illumination of a light emitting diode (LED) or generation of a service processor event message. The service processor event message may be received by a management console for the attention of a system administrator. Each alert may contain the identity of the blade server generating the alert, so that the system administrator knows which blade server(s) need to be cleaned. Automatically detecting the accumulation of dust in blade servers or other components saves time, labor, and associated operating expense as compared with manually removing and individually inspecting each blade server for dust.

Figure 1:
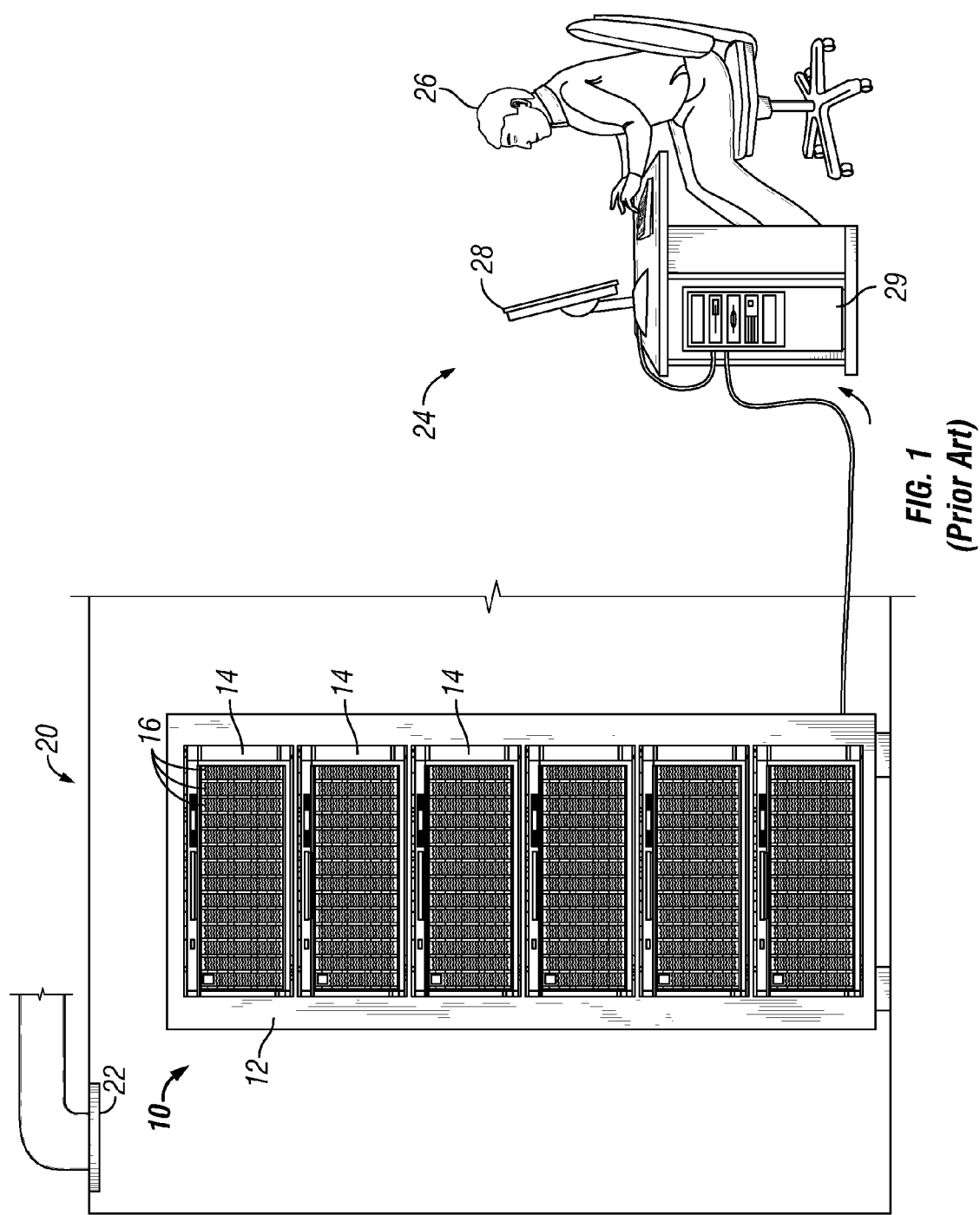
FIG. 1 is a front elevation view of a conventional rack system having a plurality of blade servers in which a dust detection system and method may be implemented.

FIG. 1 is a front elevation view of a conventional, rack-based computer system ("rack system") 10 in a data center 20. The rack system 10 is an example of a computer system having a plurality of blade servers and other air-cooled hardware devices in which dust will accumulate over time. The rack system 10 includes a rack 12 supporting six server chassis 14. Each server chassis 14 supports fourteen networked blade servers 16, along with supporting hardware, such as power supplies, switches, and a management module. Thus, the rack 12 holds up to eighty-four heat-generating blade servers and support modules, all of which are air-cooled. Periodic manual inspection of such a system may be costly and time consuming, particularly due to the large number of hardware devices involved.

Each server chassis 14 supports one or more blower module known in the art for circulating air through the server chassis 14 to cool the blade servers 16 and support modules within the server chassis 14. Heated air expelled from the rack system 10 is then taken up by an air intake 22 and circulated through a computer-room air-condition system (CRAC) that cools the air and returns it to the data center 20. As air blows through the blade servers 16 and other hardware devices, dust collects over time in each of the hardware devices in the rack system 10. The invention provides systems and methods for detecting the accumulation of dust in a blade server 16 or other hardware device without removal.

A workstation 24 is optionally networked with the blade servers 16 for helping a system administrator 26 monitor and control the blade servers 16 globally. The workstation 24 includes a management console 28, which has a customizable graphical administrative interface, and a management server 29, which can remotely control and support several remote computer subsystems including the blade servers 16. Local software (e.g. a system "agent") may be installed on each blade server 16, allowing the management server 29 to selectively interface with the various blade servers 16 to monitor and control the blade servers 16. For example, an agent installed on a particular blade server 16 may send a signal over the network to warn the system administrator 26 that intervention is required for that blade server.

The workstation 24 may include additional functionality pertaining to the detection of dust according to the invention, and that functionality may be tied in to existing features, such as the ability of the blade servers 16 to generate alerts in the form of service processor event messages. For example, each blade server 16 may detect the accumulation of dust on its components or within its housing, as further described below, and generate an alert signal when the amount of accumulated dust reaches a critical level that requires servicing the blade server 16. The alert signal may be received at the workstation 24 and reported by the management console 28. The system administrator 26 may monitor the management console 28 to know which specific hardware devices need servicing for dust removal at any particular time. This approach to monitoring the accumulation of dust within the individual hardware devices of the rack system 10 is more efficient than periodically removing and visually inspecting all the components to determine which hardware devices need cleaning.

Figure 2:
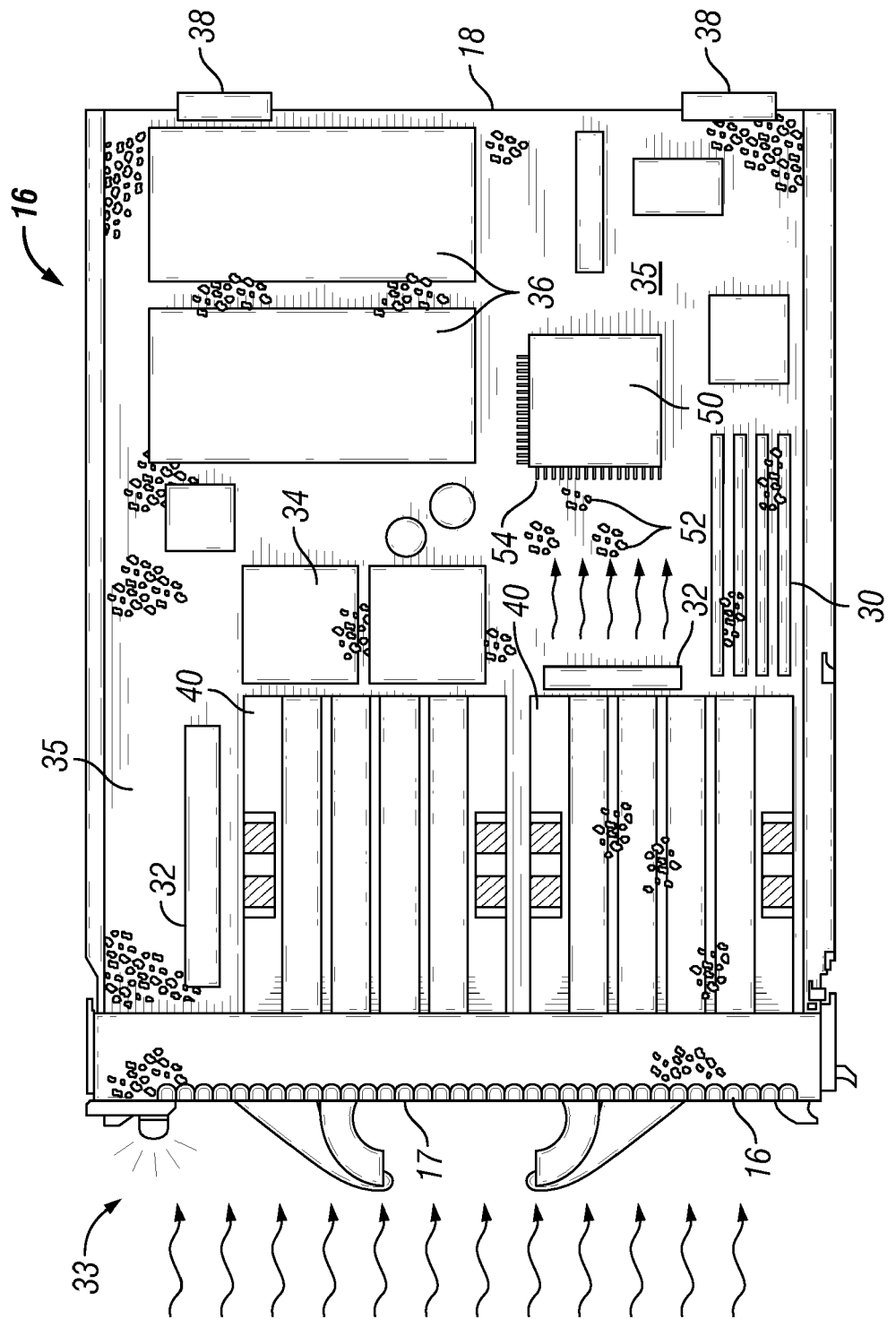
FIG. 2 is a side elevation view of one of the blade servers with an outer housing removed to reveal a dust-sensing microcontroller for sensing dust within the blade server.

FIG. 2 is a side elevation view of one of the blade servers 16 adapted to include a capacitive sensing chip 50 configured according to the invention for the detection of dust within the blade server 16. Air enters a housing of the blade server 16 at an air inlet 17 and exits at an air outlet 18. An outer housing wall has been removed to reveal some of the internal components on which dust accumulates. Some of the conventional components of the exemplary blade server 16 include four memory modules (DIMMs) 30, voltage regulators 32, control chips 34, two small form factor (SFF) hard drives 36, redundant power and signal connectors 38, and a pair of processor heatsinks 40 for cooling microprocessors ("CPUs") disposed below the heatsinks 40. The components are generally mounted on a motherboard 35. Dust accumulates in the blade server 16 and must be cleaned periodically to avoid problems. For example, the accumulation of dust reduces airflow between the fins of the heatsinks 40 and thus reduces the cooling efficiency of the heatsinks 40. This reduced cooling efficiency can impact the overall efficiency of the rack system 10, such as by requiring an increased airflow rate in order to sufficiently cool the blade servers 16.

The chip 50 is positioned on the motherboard 35. Dust 52 accumulates throughout the blade server 16, including on the input leads 54 of the chip 50. The chip 50 is configured for detecting capacitance changes induced by the accumulation of dust over time. The chip 50 is positioned on a portion of the motherboard 35 having plenty of area around the perimeter of the chip 50 unobstructed by neighboring components, so that dust-carrying airflow readily reaches the chip and deposits dust on the chip 50 over time. The dust 52 on the input leads 54 causes a change in capacitance between selected input leads, and the capacitance between the selected input leads can be correlated with the extent of dust accumulation. The chip 50 detects when dust accumulates to an excessive level, and generates an alert, such as a service processor event message and/or the illumination of an LED 33 on the front of the blade server 16.

Figure 3:
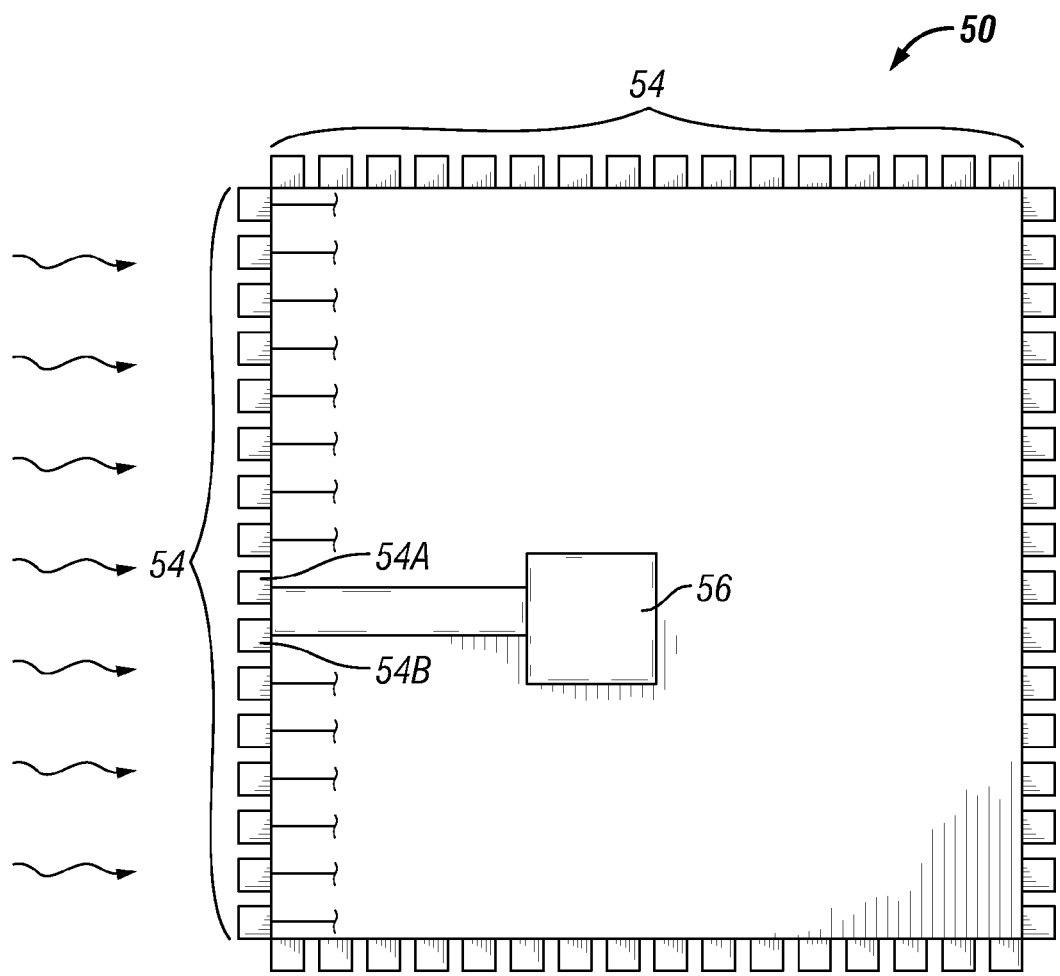
FIG. 3 is a schematic diagram of the dust-sensing microcontroller.

FIG. 3 is a schematic diagram of the chip 50. Each side of the chip 50 includes sixteen input terminals ("leads") 54, although any number of input leads may be included. The chip 50 may contain a complex architecture that includes any number of logic circuits known in the art. Different input leads 54 may be mapped to different logic circuits for inputting data used by the respective logic circuits. Among the many circuits that may be included on the chip 50 is a capacitive-sensing logic circuit outlined at 56, which is mapped to provide electronic communication with the at least two input leads 54A and 54B. As airflow passes over the capacitive input leads 54A, 54B, dust will accumulate between them. While dust may also accumulate between other input leads 54, the other input leads may be mapped to other logic circuits that are not associated with detecting the accumulation of dust.

Figure 4:
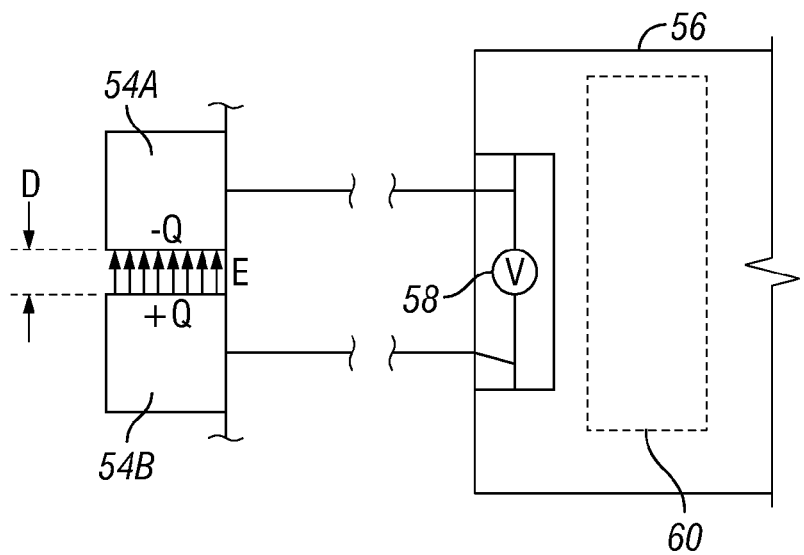
FIG. 4 is a schematic diagram of a portion of the microcontroller that includes the capacitance sensor coupled to two of the input leads.

FIG. 4 is a further detailed schematic diagram of a portion of the chip 50 that includes the capacitive input leads 54A, 54B and the capacitive sensing logic circuit 56 in electronic communication with the capacitive input leads 54A, 54B. The capacitive input leads 54A, 54B function as capacitive plates. A voltage source 58 included with the capacitive-sensing circuit 56 generates an electric field E between the capacitive input leads 54A, 54B. The electric field E results in a net negative charge "Q−" on the first input lead 54A and a net positive charge "Q+" on the second input lead 54B. The first and second input leads are spaced apart at a distance "D" that is preferably no more than about 1 mm. In many configurations, a spacing of 1 mm will allow average sized dust particles to induce a detectable change in capacitance. However, depending on the environment, the spacing may be greater or less than 1 mm. For example, dust particle size may vary between different environments, which may affect the spacing selected for the respective environment to optimize the detection of the dust particles on or between the capacitive input leads 54A, 54B. However, the voltage available on the chip may also be a factor in determining a suitable spacing of the leads.

Sensor firmware 60 may be included with the chip 56 for monitoring electrical activity at the capacitive input leads 54A, 54B and interpreting the electrical activity as a corresponding capacitance value or change in capacitance. The firmware 60 is particularly adapted for detecting changes in capacitance indicative of the presence of dust. The firmware 60 may have the ability to differentiate between capacitance changes caused by dust and capacitance changes caused by other environmental parameters, such as an accidental short or the placing of a user's finger on the input leads. For example, the chip 56 may be calibrated to establish the normal range in capacitance due to dust, so that in use, the chip 56 is responsive to changes caused by dust. Capacitance values outside this range may be selectively excluded from the analysis, or may trigger fault circuitry (not shown) to generate a fault for the attention of an administrator.

Figure 5:
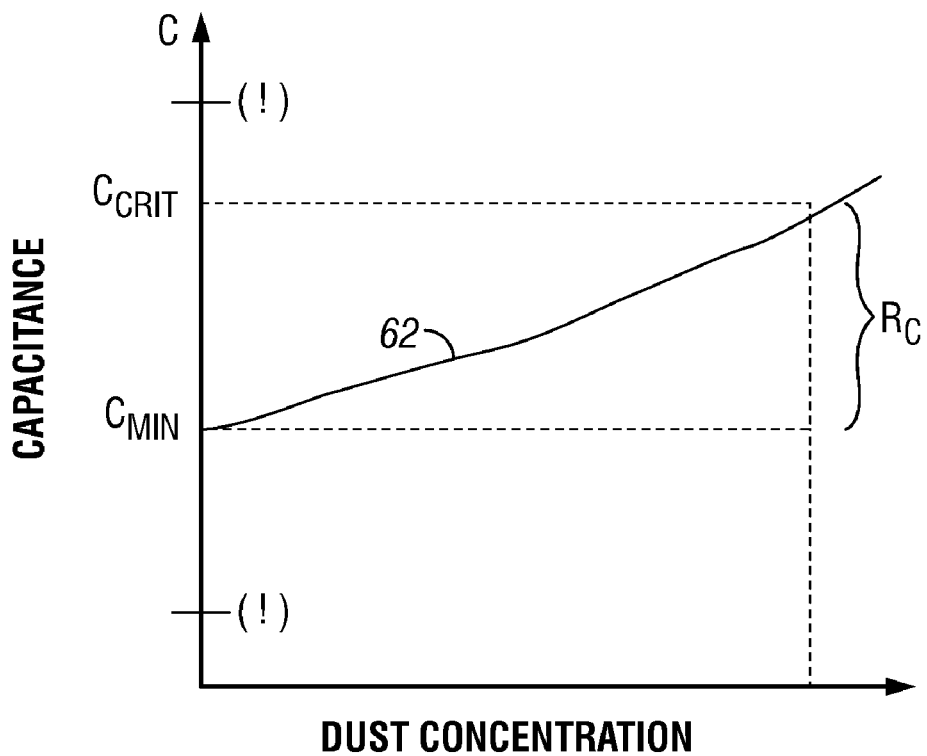
FIG. 5 is a graph of the relationship between dust accumulation and capacitance.

FIG. 5 is a graph illustrating how capacitance C between the capacitive input leads 54A, 54B might vary as a function of the amount of dust that has accumulated. An upwardly sloping curve 62 indicates a general increase in C in response to dust accumulation. The curve 62 is provided for the purpose of discussion, and an actual curve characterizing a particular chip may have a different shape. As dust accumulates, the capacitance C increases from a finite, non-zero value $C_0$ prior to the accumulation of any dust, to a critical capacitance $C_{CRIT}$ at which the device should be removed for cleaning. $C_{CRIT}$ may be selected by a system designer. $C_{CRIT}$ may be determined empirically, such as by using conventional criteria (e.g. conventional visual indicators) to determine when an excessive amount of dust has accumulated on a representative motherboard, and setting $C_{CRIT}$ as the value of C observed at that dust level.

$C_{CRIT}$ may be used in the selection of a setpoint. When a device having the chip is subsequently placed in service, an alert may be generated when C reaches or exceeds $C_{CRIT}$. Alternatively, the setpoint may be selected as a capacitance differential equal to the range "$R_C$" between $C_0$ and $C_{CRIT}$, so that an increase in capacitance equal to or greater than $R_C$ may trigger an alert. However, values significantly outside the range $R_C$ may indicate something other than the accumulation of dust. For example, an observed value of C that is significantly above $C_{CRIT}$ or below $C_0$ may indicate the presence of a foreign object, such as a finger or a short circuit between capacitive input leads. Special alerts may be generated to flag an abnormal capacitance reading such as these and differentiate these alerts from other system alerts generated in response to reaching or exceeding the capacitance setpoint.

Figure 6:
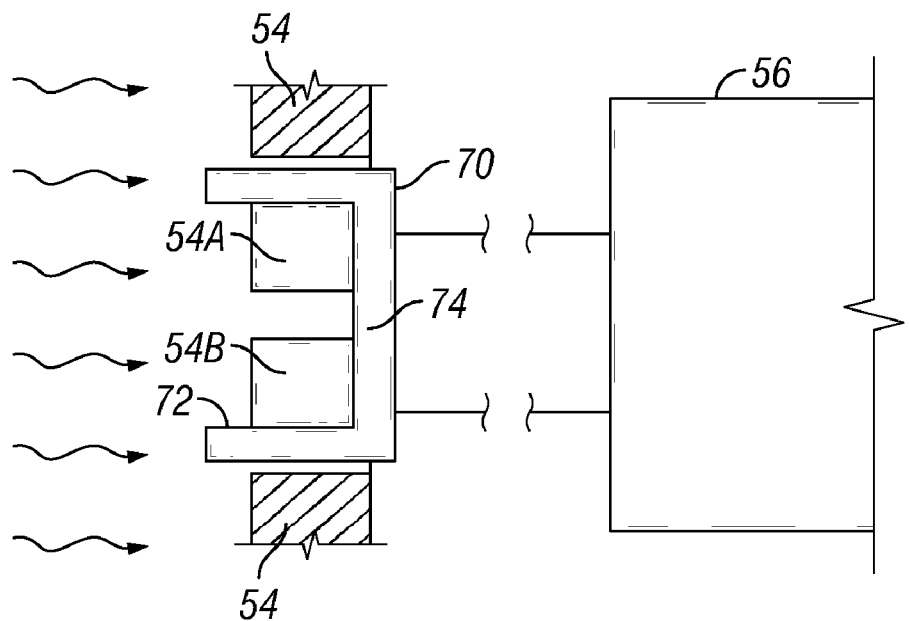
FIG. 6 is a schematic diagram of a portion of the microcontroller that includes a U-shaped projection for trapping dust on the capacitive input leads.

FIG. 6 is a schematic diagram of a portion of the chip 50 provided in FIG. 4, with some additional features. Non-participating leads (leads that are not involved in sensing capacitance) are indicated by hatching. An optional insulating material may be provided on these non-participating input leads. The capacitive input leads 54A, 54B (the leads that are involved in sensing capacitance) are indicated by the absence of hatching. The capacitive input leads 54A, 54B should be exposed to the flow of air, so that they are sensitive to the accumulation of dust. An optional U-shaped projection 70 is also provided about the exposed capacitive input leads 54A, 54B. The U-shaped projection 70 may project upwardly (out of the page) up to a few millimeters, and serves at least two purposes. First, the U-shaped projection 70 protects capacitive input leads 54A, 54B from short circuiting with adjacent components or becoming physically damaged. Second, the U-shaped projection 70 helps trap dust on the capacitive input leads 54A, 54B. The open end 72 of the U-shaped projection 70 is open to airflow (facing upstream), so that dust may enter the U-shaped projection 70. The closed end 74 is downstream, for "trapping" dust. The optional U-shaped projection 70 thereby helps collect dust over the capacitive input leads 54A, 54B, which may increase the range $R_C$ between $C_0$ and $C_{CRIT}$ (see FIG. 5). The increased range $R_C$ may help the chip 56 discern the accumulation of dust as it approaches an excesses level. This, in turn, may provide more reliable alerts. Furthermore, the projection 70 may shield the capacitive input leads 54A, 54B from interference due to other adjacent leads 54.

Figure 7:
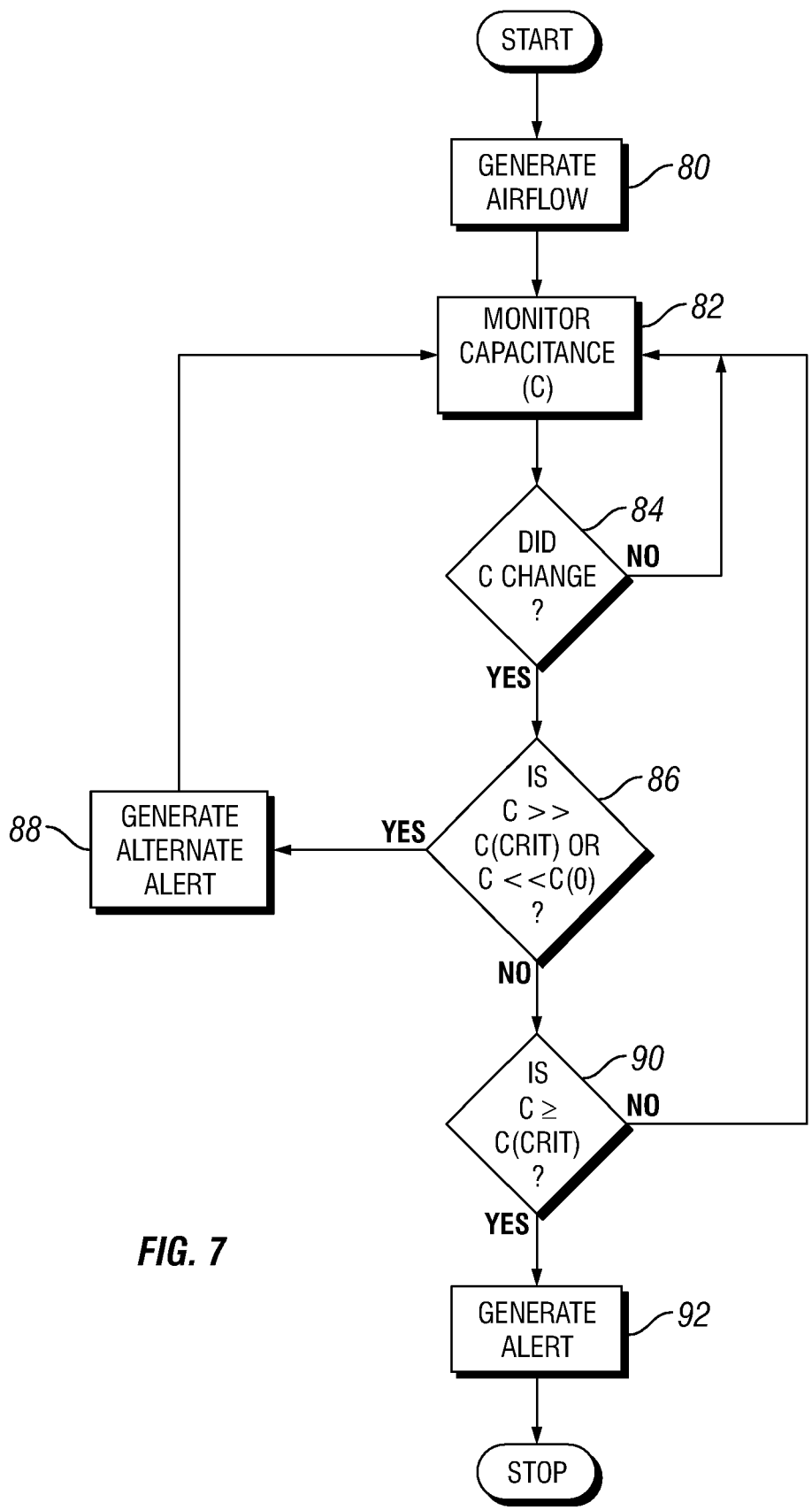
FIG. 7 is a flowchart generally outlining a method of detecting dust in a hardware device using a capacitive-sensing microcontroller.

FIG. 7 is a flowchart generally outlining a method for detecting dust within a hardware device according to the invention. Airflow is generated in step 80. For example, in a standalone PC, airflow may be generated by an on-board fan. In a multi-server rack system, airflow may be generated by a blower module supported on the multi-server chassis. Capacitance between two input leads of a chip is monitored in step 82. If a change in capacitance is detected in step 84, the change is further analyzed. If the change resulted in the value of C being very far outside the usual range $R_C$, such as much greater than $C_{CRIT}$ or much less than $C_0$ as set out in step 86, then some cause other than a gradual accumulation of dust may be suspected. The anomaly could be a short circuit of the capacitive input leads, for example. An "alternative alert" is generated in step 88 to indicate this condition. However, assuming the value of C has not moved appreciably outside the usual range, the capacitance may instead be monitored for routine changes due to the accumulation of dust. Once C reaches or slightly exceeds $C_{CRIT}$, as determined in step 90, then an alert may be generated in step 92 indicating the accumulation of dust and the need to service the device for dust removal.

The above described embodiments are non-limiting examples of how a dust detection system and method may be implemented, and other embodiments of capacitive dust sensing are within the scope of the invention. A dust detection system as shown and described herein is useful in virtually any electronic system prone to the accumulation of dust. Almost any electronic system may benefit from the ability to automatically, electronically detect the accumulation of dust. Electronic systems having a capacitive dust detection system according to the invention will require much less manual, labor-intensive inspection, with an associated reduction in downtime and maintenance expenses. Electronic systems may be serviced for dust removal and general cleaning on a more logical, as-needed basis, rather than as a matter of routine. For example, system administrators responsible for larger computer systems may spend less time manually inspecting and servicing blade servers and other hardware devices, and may instead respond as needed to alerts individually generated by the blade servers. Thus, system resources are better allocated to those tasks and devices with a demonstrable need for attention. Furthermore, since the dust accumulation is detected using features built into a chip, it is not necessary to provide additional components in the housing or on the motherboards.

The terms "comprising," "including," and "having," as used in the claims and specification herein, shall be considered as indicating an open group that may include other elements not specified. The terms "a," "an," and the singular forms of words shall be taken to include the plural form of the same words, such that the terms mean that one or more of something is provided. The term "one" or "single" may be used to indicate that one and only one of something is intended. Similarly, other specific integer values, such as "two," may be used when a specific number of things is intended. The terms "preferably," "preferred," "prefer," "optionally," "may," and similar terms are used to indicate that an item, condition or step being referred to is an optional (not required) feature of the invention.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

What is claimed is:

1. A dust detection system for detecting the accumulation of dust in an air-cooled hardware device, comprising:
    a device housing having an air inlet and an air outlet;
    an airflow source for generating airflow through the device housing from the air inlet to the air outlet; and
    a microcontroller disposed in the device housing, the microcontroller including a plurality of input leads and a built-in capacitance sensor configured for generating a signal in relation to the capacitance between at least two of the input leads, wherein the capacitance sensor is sensitive to accumulation of dust between the at least two input leads.

2. The dust detection system of claim 1, wherein the microcontroller is configured for generating the signal in response to the value of the capacitance between the at least two input leads reaching or exceeding a capacitance setpoint.

3. The dust detection system of claim 1, wherein the signal comprises illumination of a light emitting diode or a service processor event message.

4. The dust detection system of claim 1, wherein the at least two input leads associated with the capacitance sensor are spaced within about 1 millimeter.

5. The dust detection system of claim 1, wherein the at least two input leads associated with the capacitance sensor are positioned upstream of the body of the microcontroller with respect to a direction of airflow from the airflow inlet to the airflow outlet of the device housing.

6. The dust detection system of claim 1, wherein the air-cooled hardware device comprises an air-cooled server removably insertable into a multi-server chassis.

7. The dust detection system of claim 6, further comprising a management module disposed in the chassis and in communication with the server for receiving the signal and identifying the hardware device.

8. The dust detection system of claim 1, further comprising a raised portion about the at least two input leads for trapping dust on the at least two input leads.

9. The dust detection system of claim 8, wherein the raised portion is substantially U-shaped, with an open end of the U-shaped projection is positioned upstream from a closed end of the U-shaped projection.

10. The dust detection system of claim 1, wherein electrically conducting portions of the at least two input leads are exposed to the airflow, and the other of the plurality of input leads are electrically insulated from airflow.

11. A method of detecting dust within a hardware device, comprising:
    generating airflow through a housing of the hardware device;
    sensing the capacitance between at least two input leads of a microcontroller disposed within the hardware device;
    detecting a change in capacitance between the at least two leads consistent with the deposition of dust between the leads; and
    generating a signal responsive to the change in capacitance.

12. The method of claim 11, further comprising generating the signal in response to the capacitance reaching or exceeding a setpoint.

13. The method of claim 12, further comprising generating an alert in response to reaching or exceeding the capacitance setpoint.

14. The method of claim 13, wherein generating the alert comprises illuminating an LED or generating a service processor event message.

* * * * *